(12) United States Patent
Dakak

(10) Patent No.: US 10,625,059 B2
(45) Date of Patent: Apr. 21, 2020

(54) ANGIOPLASTY, SELF-EXPANDING, STENT CATHETER WITH LOW PRESSURE ANCHOR AND/OR MARKER BALLOON ASSEMBLY AND METHOD

(71) Applicant: Nadar A. Dakak, Potomac, MD (US)

(72) Inventor: Nadar A. Dakak, Potomac, MD (US)

( * ) Notice: Subject to any disclaimer, the term of this patent is extended or adjusted under 35 U.S.C. 154(b) by 75 days.

(21) Appl. No.: 15/019,237

(22) Filed: Feb. 9, 2016

(65) Prior Publication Data

US 2017/0326344 A1    Nov. 16, 2017

(51) Int. Cl.
| | |
|---|---|
| A61M 25/10 | (2013.01) |
| A61M 29/02 | (2006.01) |
| A61F 2/962 | (2013.01) |
| A61F 2/95 | (2013.01) |
| A61F 2/958 | (2013.01) |

(52) U.S. Cl.
CPC ............. *A61M 25/104* (2013.01); *A61F 2/95* (2013.01); *A61F 2/962* (2013.01); *A61M 29/02* (2013.01); *A61F 2/958* (2013.01); *A61F 2002/9534* (2013.01); *A61M 2029/025* (2013.01)

(58) Field of Classification Search
CPC ................ A61M 25/104; A61M 29/02; A61M 2029/025; A61F 2/95; A61F 2/962; A61F 2/958; A61F 2002/9534
See application file for complete search history.

(56) References Cited

U.S. PATENT DOCUMENTS

| | | | |
|---|---|---|---|
| 5,607,444 A | 3/1997 | Lam | |
| 2005/0137690 A1* | 6/2005 | Salahieh | A61F 2/2418 623/2.11 |
| 2005/0273060 A1* | 12/2005 | Levy | A61B 17/1114 604/192 |
| 2007/0173784 A1 | 7/2007 | Johansson et al. | |
| 2007/0270935 A1 | 11/2007 | Newhauser et al. | |
| 2007/0293935 A1* | 12/2007 | Olsen | A61F 2/95 623/1.12 |
| 2008/0086083 A1 | 4/2008 | Towler | |
| 2008/0208307 A1 | 8/2008 | Ben-Muvhar et al. | |
| 2008/0243233 A1 | 10/2008 | Ben-Muvhar et al. | |
| 2009/0043194 A1 | 2/2009 | Barbut | |
| 2014/0194920 A1* | 7/2014 | Krahbichler | A61F 2/013 606/200 |

OTHER PUBLICATIONS

Radiopaedia Iliac artery article retrieved Jun. 11, 2019 (evidence article).*
US National Library of Medicine National Institutes of Health Aortic Dimension article retrieved Jun. 11, 2019 (evidence article).*

* cited by examiner

*Primary Examiner* — Erich G Herbermann
(74) *Attorney, Agent, or Firm* — Scott Houtteman; Bradford E. Kile; Houtteman Law LLC

(57) ABSTRACT

An angioplasty apparatus and method, with a self-expanding stent, for facilitating accurate placement of the self-expanding stent for dilating a patient's blood lumen stenosis, the apparatus includes arcuate, low pressure, balloon segment(s) connected at a distal end of a deployment catheter assembly with axial gap(s) to facilitate continuous blood flow during a stenting procedure.

14 Claims, 4 Drawing Sheets

ANGIOPLASTY, SELF-EXPANDING, STENT CATHETER WITH LOW PRESSURE ANCHOR AND/OR MARKER BALLOON ASSEMBLY AND METHOD

RELATED APPLICATION

This application relates to co-pending applications entitled "Angioplasty Marker and Guide Catheter With Bifurcation Site Stenting, Apparatus and Method" Ser. No. 15/019,183 and "Angioplasty Anchor and/or Marker Balloon Stent Catheter Apparatus and Method," Ser. No. 15/019,207 both of common inventorship and ownership as the present application and as filed on an even date herewith. The disclosure of these co-pending applications are incorporated herein by reference as though set forth at length.

BACKGROUND OF THE DISCLOSURE

This invention relates to a self-expanding stent catheter with a low pressure, anchor and/or marker balloon assembly within the field of peripheral angioplasty. More specifically, this invention relates to accurate stent placement of a self-expanding stent for deployment at a stenotic segment site within a patient's vascular system while concomitantly maintaining lumen blood flow during an angioplasty stenting procedure.

The vascular bed in humans is a complex and an extensive network of lumens carrying blood and delivering oxygen and nutrients throughout the skeletal network, organs and muscle tissues of the body. At a macro level the human circulatory system can be logically characterized as originating from the heart with an initially ascending aorta arch extending from the left ventricle upwardly and then descending generally vertically downward via a central lumen column through a patient's thoracic region and diaphragm to an abdominal aorta segment. The aorta terminates into common left and right iliac arteries extending down into lower extremities. In broad brush terms a sequence of blood flow is from a left heart ventricle to the aorta, to arteries, to arterioles, to venules, to veins, and to a vena cava back to a right side of the heart.

The aorta provides a base for systemic circulation of blood for the entire body. Right and left coronary branches extend from an aortic root to supply a patient's heart while the aortic arch supplies blood to the patient's head, neck and arms. Branches from the thoracic aorta supply the chest and branches from the abdominal aorta supply the abdomen while the pelvis and lower extremities are fed from common iliac arteries extending from a base region of the aorta.

Vascular lumens are composed of elastic tissue which can, over time, become somewhat hardened in a disease zone due to an internal accumulation of cholesterol laden plaque, which is a fatty material composed of cholesterol and other particles which build up within an artery wall to create a narrowing (stenosis) of the artery. Plaque stenotic segments can decrease vessel elasticity and concomitantly impair blood flow and in acute instances even occlude a free flow of blood through the lumen. This malady is sometimes referred to as atherosclerotic arterial disease.

In 1964 an vascular radiologist by the name of Charles Dotter, often referred to as the "Father of Interventional Radiology" pioneered development of angioplasty and a catheter delivered stent as a treatment for peripheral arterial disease.

Stents are now universally used in percutaneous coronary and peripheral angioplasty procedures, which effectively open narrowed blood vessels. A stent is a tiny, expandable, cylindrical wire mesh scaffolding. A stent may be formed as a cylindrical, self-expanding unit which is delivered to a stenotic site in a collapsed posture within a covering retention sheath or collar. Once the stent is in position the sheath or collar is axially withdrawn and the self-expanding stent radially extends and compresses a stenotic site within a patient's diseased lumen.

An interventional physician uses radiography, an X-ray procedure, to identify a stenosis location and estimates the size of a diseased blood vessel and severity of stenotic plaque narrowing. Blood vessels are not visible by X-ray, per se, however, by injecting a contrast media (dye) through a catheter sheath a trained physician is capable of accurately viewing arterial boundaries with the pulsating flow of blood through downstream arteries and develop an accurate sense of a stenotic site requiring interventional correction.

Placing a stent at a site of a stenosis in a downstream segment of a blood vessel is a routine process performed by an interventional physician; however, placing a stent when the stenosis is at a bifurcation, is complex. Positioning a stent too distal may miss part of a narrowing stenosis while positioning a stent too proximal may result in proximal end of the stent protruding into a primary blood vessel.

Accurately and effectively addressing a plaque stenosis at certain sites within a human circulatory system can be challenging. One region of special interest is peripheral angioplasty with stenting to osteal and proximal segments of the iliac arteries.

It is not uncommon, to encounter stenotic disease at the abdominal aortic bifurcation which might involve both iliac arteries. Angioplasty in this instance may require advancing self-expanding stents, from both common femoral arteries, one from each side, into the lower abdominal aorta, with simultaneous expansion of both self-expanding stents (kissing stents), creating two channels in the abdominal aorta, one into each iliac artery.

The result in such bilateral procedures are usually effective and the obstruction resolves. Allowing distal stent struts in the abdominal aorta, however, may hinder future peripheral intervention when a physician elects a cross over approach. In the cross over approach, angioplasty is carried out using the common femoral access to fix a blockage in the contralateral lower extremity. In this case a stiff guide wire is introduced from the right or the left common femoral arteries, into the abdominal aorta and down to the contralateral iliac and femoral vessels. A long vascular sheath is introduced over the wire, across the abdominal aortic bifurcation, into the contralateral side. The peripheral angioplasty is therefore carried out using the right access to the left lower extremity and vice versa.

Having the stent struts, in the abdominal aorta from a previous angioplasty to the iliac vessels, would eliminate the future option of contralateral approach, forcing an interventional physician to access the lower extremity through an upper extremities, a more complex risky and prolonged approach which may not be possible. Alternatively a patient may be subjected to an operative procedure for lower extremities vascular surgery.

Proper positioning of the stents at the opening of the iliac arteries, using an anchor and marker fluid in the anchor balloon or balloons at the distal end of the stent, will minimize stent strut protrusion into the abdominal aorta and thus will keep the option of future crossover peripheral angioplasty approach available.

The limitations suggested in the preceding are not intended to be exhaustive but rather are among many which may tend to reduce the effectiveness, reliability and physician satisfaction with prior methods and apparatus for angioplasty, with stenting, at stenotic sites within a patient's vascular system. Other noteworthy problems may also exist; however, those presented above should be sufficient to demonstrate that present angioplasty methods and apparatus, involving stenting a stenotic lumen in a patient's circulatory system, appearing in the past, will admit to worthwhile improvement.

THE DRAWINGS

Numerous advantages of the present invention will become apparent from the following detailed description of an illustrative embodiment taken in conjunction with the accompanying drawings wherein.

Figure 1:
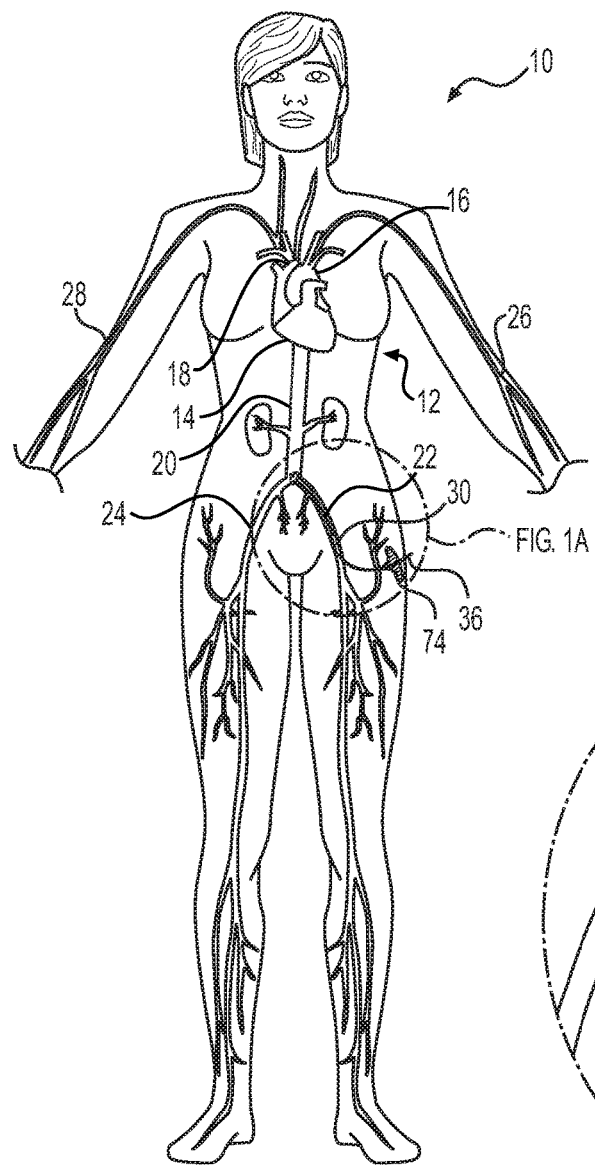
FIG. 1 is a human silhouette, front view, including basic illustrative components of a human heart and vascular system with an ipsilateral insertion of a self-expanding stent deployment sheath into a patient's left common femoral artery to address a patient's stenotic lesion above the point of insertion such as the junction of a patient's left iliac artery and base of the aorta.
Figure 1A:
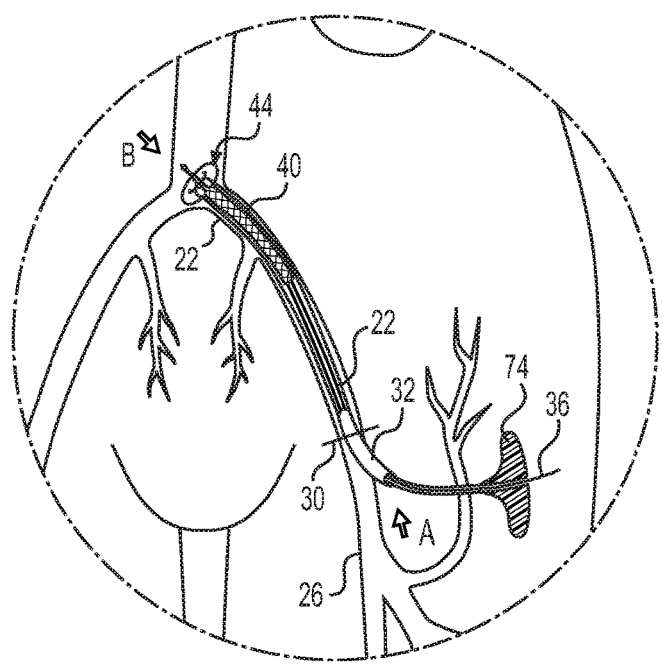
FIG. 1A is an enlargement bubble disclosing detail of the ipsilateral insertion, in the general direction of arrow "A", of a self-expanding, stent catheter with an anchor and/or marker balloon assembly positioned at a junction of the base of a patient's aorta and the left iliac artery.
Figure 3:
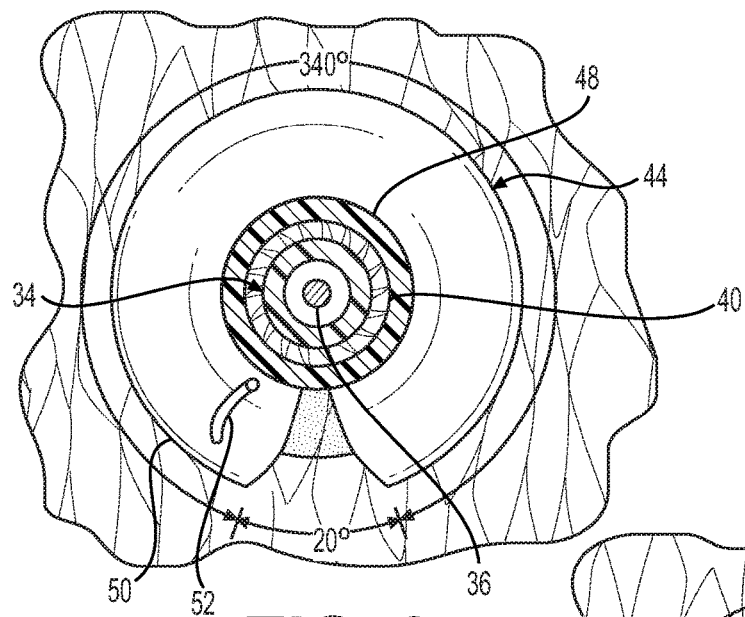
Figure 4:
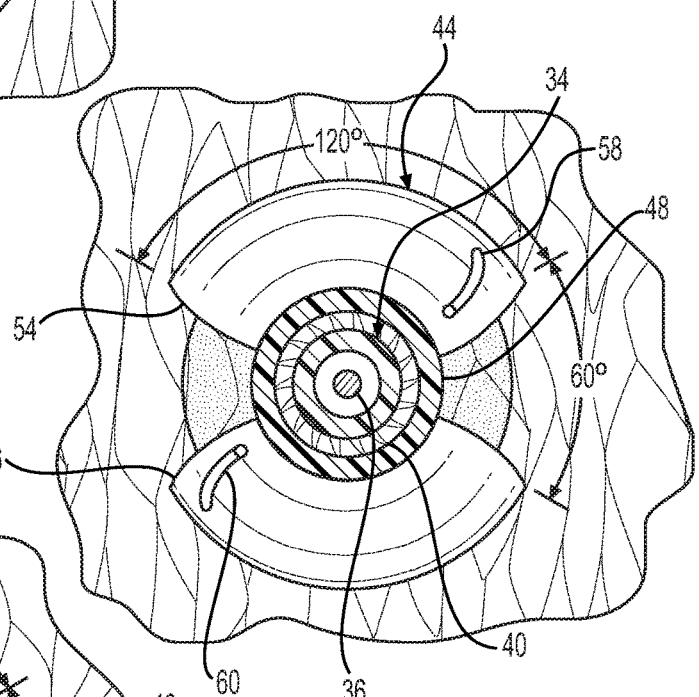
Figure 5:
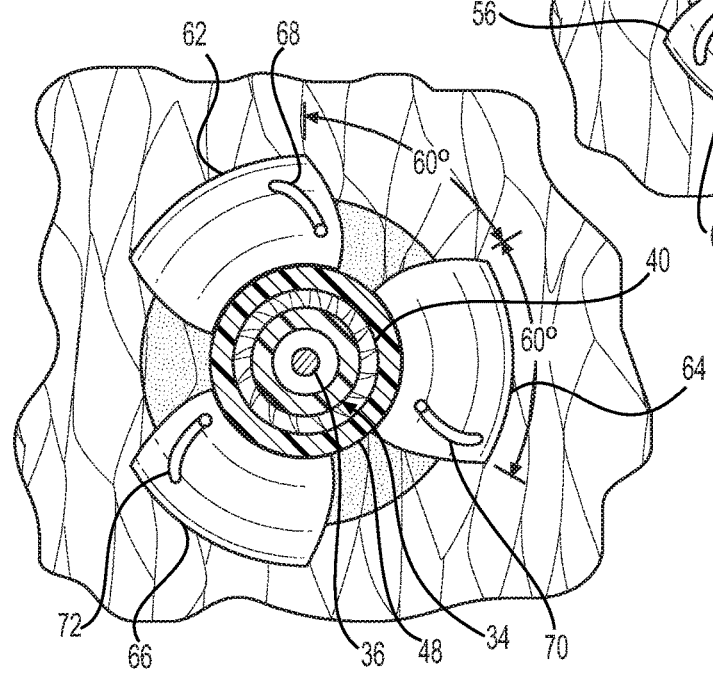
Figure 6:
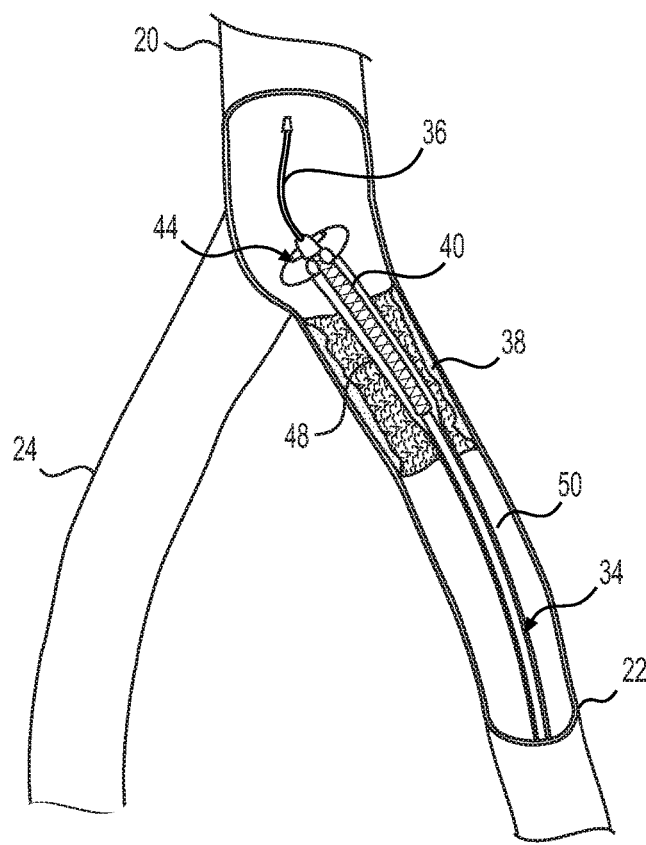
Figure 7:
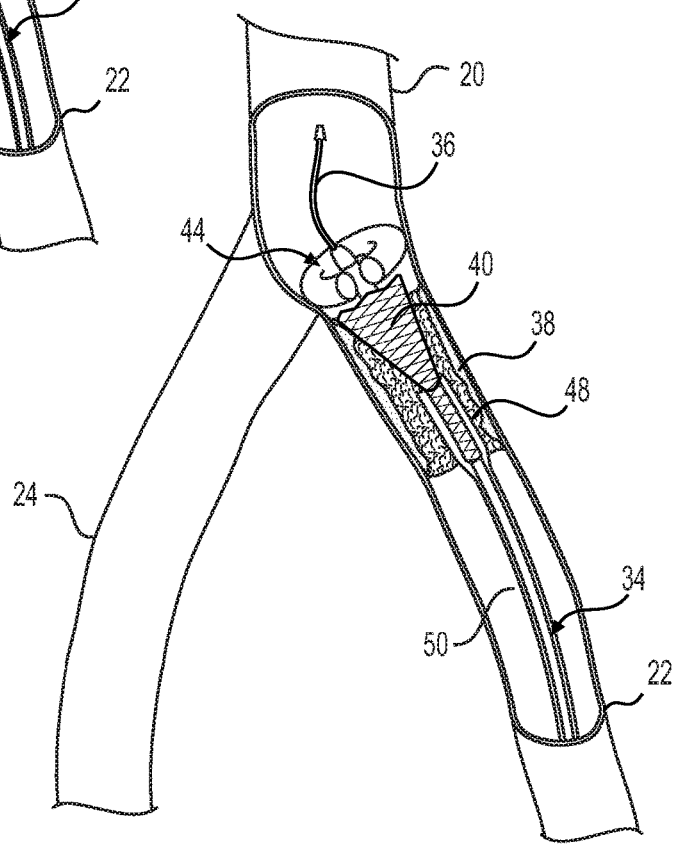

FIG. 3 is an axial view, taken in the general direction of arrow "B" in FIG. 1A of a patient's stenotic lumen with a self-expanding stent and an anchor and/or marker balloon segment, taken in partial cross-section with a distal to proximal perspective, disclosing one embodiment of the invention including a single low pressure anchor and/or marker balloon arcute segment of approximately 340° with a circumferential gap of 20° to permit a continuous flow of blood and/or contrast media past the deployed low pressure, anchor and/or marker balloon assembly during a stenting procedure. In this view and in the views of FIGS. 4 and 5 cross-sectional components of a self-expanding, metal stent are shown in full line view, for purposes of illustration, even though one of skill in the art will recognize that portions of these components are operably behind low pressure, anchor and/or marker balloon segment(s);

FIG. 4 is a view similar to FIG. 3 disclosing an alternative preferred embodiment of the invention with a pair of opposing anchor balloon segments with each segment subtending an arc of approximately 120° to provide opposing axial passages of approximately 60° degrees to facilitate a continuous flow of blood and/or contrast media past the anchor balloon segments during a stenting procedure;

FIG. 5 is a view similar to FIGS. 3 and 4 disclosing yet another preferred embodiment of the invention where three generally equal anchor balloon arcuate segments of approximately 60° are illustrated positioned about a self-expanding stent deployment sheath to advantageously maintain lumen blood and/or contrast media flow during a stenting procedure;

FIG. 6 is a partial, cross-sectional, view of an illustrative stenosis site within a patient's left iliac artery at the junction with the base of the patient's aorta showing insertion of a collapsed anchor and/or marker balloon segment(s) and an outer sheath covering a self-expanding stent; and FIG. 7 is a partial, cross-sectional, view similar to FIG. 6 illustrating initial deployment of a self-expanding stent, by withdrawing on site a retention collar with a low pressure, anchor and/or marker balloon assembly deployed at a position adjacent a bifurcation stenosis site to be treated.

DETAILED DESCRIPTION

In this description and in the claims the expressions "approximately" or "generally" are intended to mean at or near but not always exactly such that an exact dimension or location is not considered critical in contexts where those expressions appear, unless specifically stated otherwise. In this description focus will be directed to a vascular, self-expanding stent mounted upon a deployment catheter sheath with a low pressure, anchor and/or marker balloon segment or segments for angioplasty stenting at a stenotic bifurcation location at the base of a patient's aorta. The term low pressure means generally one to two atmospheres of fluid pressure as opposed to nine to eighteen atmospheres of pressure which is often used in some stent, expansion balloon, angioplasty contexts and procedures.

Referring initially to FIGS. 1 and 1A there is shown a front silhouette view of a human FIG. 10 with a generalized and illustrative outline of basic components of a human circulatory system 12 including a heart 14, an ascending aorta 16 connected to a left ventricle of the heart, an aorta arch 18 and a descending central abdominal aorta 20. The human body has a number of arteries stemming from the aorta but for purposes of this description only the left 22 and right 24 iliac arteries descending into a patient's legs are depicted as being representative.

In addition to the left and right iliac arteries 22 and 24 FIGS. 1 and 1A generally depict left and right common femoral arteries extending into a patient's lower extremities; as well as left 26 and right 28 brachial arteries in the figure's arms.

One percutaneous entry site for angioplasty, with stenting, can be a patient's left leg common femoral artery at approximately location 30 shown in FIGS. 1 and 1A. Other entry sites are contemplated by the subject invention and sites 30 is intended for purposes of illustration and not limitation. Briefly, in this, entry from the common femoral artery 26, up against the flow of blood (called a retrograde approach) can be used to address an ipsilateral lesion in the iliac artery 22, for example. There is a different illustrative approach when the insertion from the common femoral artery is pointing down (ante-grade approach) to fix a lesion downstream in the same leg.

Referring now specifically to FIG. 1A a common femoral site 30 is shown that receives a deployment entry sheath 32 that projects a relatively short distance via a patient's common femoral artery and includes a one way check valve operable to receive a stent catheter but will block an outward flow of blood from the percutaneous entry site. A stent deployment catheter 34 is inserted through the entry sheath 32 and is axially fed over a guide wire 36. The guide wire 36 is shown extending upward in the general direction of arrow "A" within a patient's common femoral artery and through a plaque stenosis 38 to be treated, noted FIGS. 6 and 7. A wire mesh, self-expanding stent 40 is carried by the deployment catheter sheath 34 in a contracted posture for deployment at a stenotic site 38.

Figure 2:
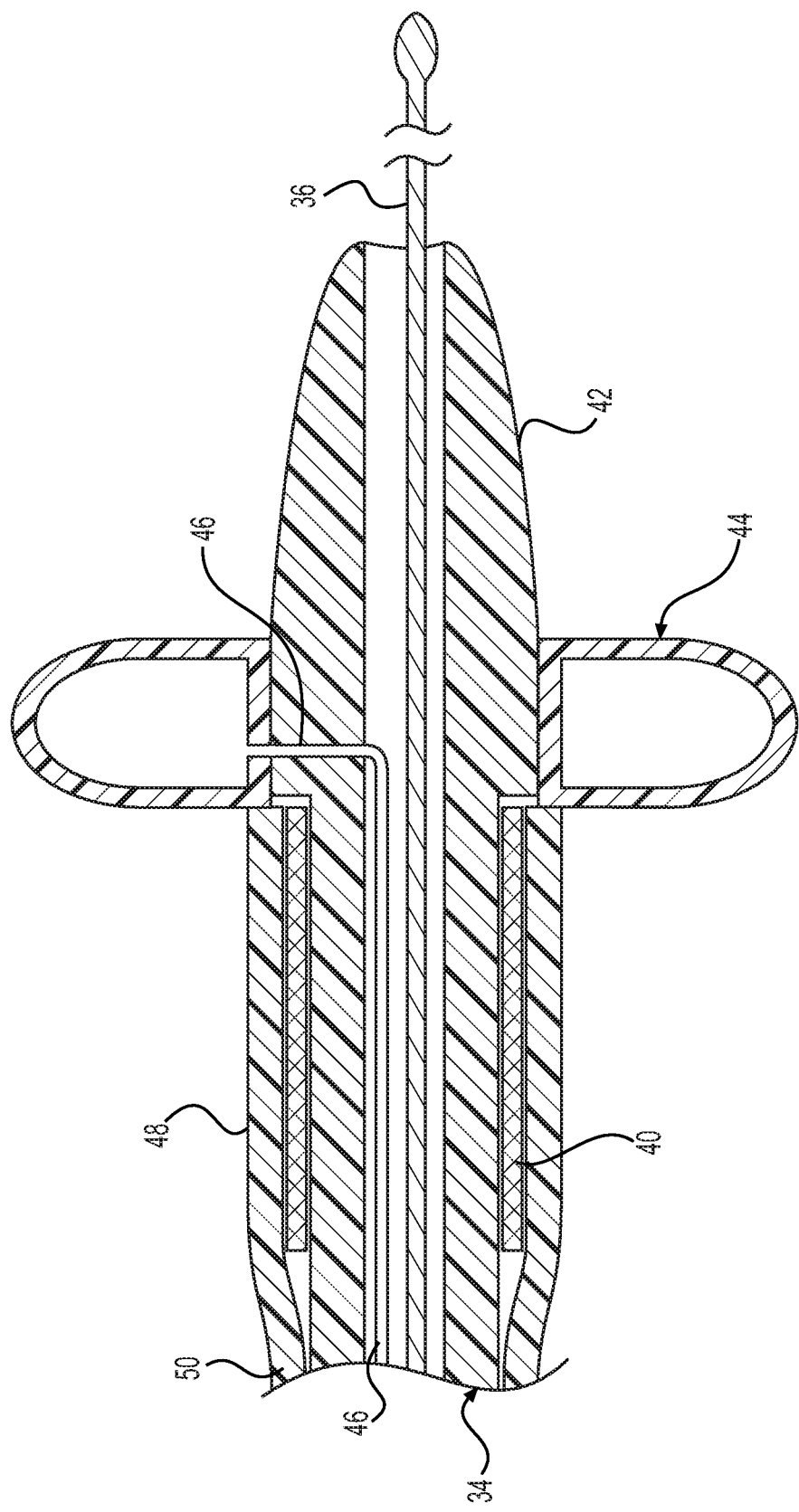
FIG. 2 is a cross-sectional, detail view of a nose portion of a deployment sheath carrying a self-expanding stent which is held in a collapsed posture by a concentric release collar or sheath.

Turning now to FIG. 2 the deployment catheter sheath 34 terminates with an insertion head 42 which is operable to facilitate deployment of a distal end of the deployment catheter sheath 34 over the guide wire 36 and through a patient's artery 22 such as depicted in FIG. 1A. The anchor and/or marker balloon assembly 44 is operably attached to the deployment catheter sheath 34 and is fitted with a fluid delivery conduit 46 as shown extending through the deployment catheter sheath 34 to deliver low pressure fluid, such as saline solution and/or marker media, into the anchor balloon assembly 44. Although a separate conduit 46 is illustrated that extends within a central passage of the deployment catheter sheath 34 the subject invention also includes creation of a passage(s) within the side wall of the deployment catheter sheath 34 or fluid passage(s) mounted on an exterior surface of the deployment catheter sheath 34 as alternate forms of selectively delivering saline and/or marker media into the interior of individual balloon segment or segments comprising the anchor and/or marker balloon assembly 44.

The self-expanding stent 40, per se, is of a conventional commercial design, and is carried generally upon a distal end of the deployment catheter sheath 34 in a collapsed condition. The self-expanding stent 40 is held in a collapsed state by a surrounding, pull back, stent retention collar 48 at a location proximal to the anchor and/or marker balloon assembly 44. An exterior, pull-back, actuation sheath 50 is integral with a proximal end of the stent retention collar 48 and extends coaxially throughout the length of the deployment catheter sheath 34. The exterior actuation sheath 50 terminates with a pullback handle 74, note FIG. 1A, for selectively withdrawing the retention collar 48 to permit the self-expanding stent 40 to radially deploy at a patient's stenotic lumen site.

FIG. 3 is an illustration of one embodiment of the anchor balloon(s) assembly 44 generally viewed in the direction of arrow "B" in FIG. 1A. In this embodiment a single low pressure, arcuate, anchor and/or marker balloon 50 is shown that preferably extends approximately three hundred and forty degrees around a distal end of the guide catheter sheath 34. The low pressure, anchor and/or marker balloon segment 50 has a small, low pressure line 52 that extends along or within the guide catheter sheath 34 and is used to selectively inflate the anchor balloon segment 50. At a location exterior to a patient's vascular system an interventional physician is able to inject low pressure fluid such as a saline solution and/or radiopaque marker media with one or two atmospheres of pressure into anchor balloon segment 50 by injection, for example, with a hand syringe (not shown). The anchor balloon will then be gently expanded into engagement with a peripheral site of a surrounding artery wall axially adjacent to a stenotic lumen site to be treated.

The anchor balloon segment 50 preferably occupies an arcuate expanse of approximately three hundred and forty degrees and there is a peripheral gap of at least approximately twenty degrees enabling blood or marker media to flow past the anchor balloon segment 50 during a stenting procedure. Although three hundred and forty degrees is one preferred embodiment of the arcuate extent of the anchor balloon segment 50 a degree of operative advantage can be realized from the subject invention where the arcuate extent of the single marker balloon segment 50 shown in FIG. 3 is as little as approximately forty-five degrees with generally three hundred and fifteen degrees of passage space around the distal end of the deployment catheter sheath 34.

FIG. 4 is a view similar to FIG. 3 but discloses an alternate preferred embodiment of the invention disclosing a low pressure anchor and/or marker balloon assembly 44 composed of two arcuate, low pressure, anchor and/or marker balloon segments 54 and 56 positioned in an opposing posture at a distal end of the guide catheter sheath 34. This balanced arrangement of arcuate, low pressure, balloon segments 54 and 56, provides an ability for an interventional physician to selectively control the amount of pressure within each balloon segment. This enhances a physician's ability to establish an approximately coaxial placement of the guide catheter sheath 34 with a patient's branch artery. In this embodiment each of the two balloon segments subtends an arc of at least one hundred degrees but less than one hundred and forty degrees and preferably one hundred and twenty degrees. The substantial combined open region of approximately eighty to one hundred and sixty degrees provides a relatively unobstructed flow of blood and/or contrast media through the patient's stenotic site during a stenting procedure.

Each of the anchor balloon arcuate segments is shown in FIG. 4, for purposes of illustration, with an independent thin tube 58 and 60 extending through, or operably along, or embedded within the side wall of the guide catheter sheath 34, as previously noted, for use in separately and selectively filling the low pressure marker balloon segments 54 and 56 respectively with a saline or radiopaque fluid by using for example a hand operated syringe. The capacity to separately inflate each anchor balloon segments enables a physician to selectively orient the end of the guide catheter sheath 34 with respect to a branch artery as necessary or desirable to facilitate a normal, or near normal, positioning of the distal end of a guide catheter sheath 34 with respect to placement at a desired branch lumen.

FIG. 5 discloses yet another preferred embodiment of the invention comprising an anchor balloon assembly 44 composed of three arcuate, low pressure, anchor and/or marker balloon segments 62, 64, and 66 and associated independent fill lines 68, 70 and 72. The fill lines may be embedded within the side wall of the deployment catheter sheath 34 or deployed within the interior or affixed to the exterior of the sheath as operably desirable. This enables transmission of a low pressure saline or radiopaque marker media to be selectively injected into the individual anchor balloon segments with variable pressure via a hand syringe from a proximal end of the guide catheter sheath 34.

The anchor balloon segments 62, 64 and 66 each extend peripherally around a distal end of the deployment catheter sheath 34 at least approximately twenty degrees but less than approximately one hundred degrees and preferably sixty degrees. In this embodiment it is preferred, and as illustrated, there is symmetric positioning of the anchor and/or marker balloon segments. This preferred balloon segment spacing concomitantly provides a degree of open space for blood and contrast media flow during a stenting procedure. Moreover, with three independent pressure zones there is an enhanced positioning capability of a distal end of a guide catheter sheath 34 with respect to a branch artery by appropriate selection of pressure within each marker balloon segment. In addition, although symmetric placement of the anchor balloon segments 62, 64 and 66 is illustrated, in certain patient anatomic configurations the subject invention envisions asymmetric mounting of the anchor and/or marker balloons upon generally a distal end of the guide catheter sheath 34.

FIGS. 6 and 7 disclose a stenting procedure sequence in accordance with one preferred embodiment of the invention. In this, FIGS. 1, 1A and 6 depict an ipsilateral insertion of a deployment catheter sheath 34 via a patient's left common femoral artery and into the patient's iliac artery below a stenotic site to be treated. A guide wire 36 is coaxially extended through the deployment sheath 34 and through a patient's artery 22, past a stenotic site 38 to be treated.

Insertion of the guide wire 36 is followed by extending the deployment catheter sheath 34 along the guide wire with a self-expanding stent 40, carried at a distal end of the deployment catheter sheath 34, in a collapsed posture, through the stenosis 38 to be addressed.

From the posture of the proximal end of the deployment catheter sheath 34, depicted in FIG. 6, one or more syringes are used to selectively inflate the low pressure anchor balloon segment or segments 50 with a saline solution and/or radiopaque marker media and the inflated anchor balloon segment or segments are then drawn back into a posture adjacent a distal end of a stenotic bifurcation site 38 to be treated.

As illustrated in FIGS. 1A and 7, when a distal end of the self-expanding stent 40 is anchored in position by expansion of the anchor balloon assembly 44 an interventional physician operably uses a handle 74 to draw back outer sheath 50 which is directly coupled to the stent retention collar 48. The self-expanding stent 40 then deploys and radially compresses the stenotic lesion 38 to restore an acceptable flow of blood through the patient's artery.

Once the stent 40 is fully deployed the anchor balloon assembly 44 is collapsed and the deployment catheter sheath 34, guide wire 36 and collapsed anchor balloon assembly 44 are withdrawn ipsi-laterally.

In certain instances the self-expanding stent 40 may not fully radially expand as intended. If that occurs a conventional balloon catheter may be independently inserted and inflated within the stent to assist in full radial expansion of the self-expanding stent, scaffolding, structure 40.

In describing the invention, reference has been made to preferred embodiments. Those skilled in the art however, and familiar with the disclosure of the subject invention, may recognize additions, deletions, substitutions, modifications and/or other changes which will fall within the scope of the invention as defined in the following claims.

What is claimed is:

1. An angioplasty self-expanding stent catheter apparatus including at least one of a low pressure marker balloon assembly for facilitating accurate placement of a self-expanding stent within a patient's stenotic lumen site, said site located in an iliac artery at the point where the iliac artery branches from a base of an aorta, said angioplasty self-expanding stent catheter apparatus comprising: a deployment catheter sheath having a proximal end and a distal end and being operable to be extended over a guide wire during a patient stenting procedure; a self-expanding stent connected generally at a distal end of said deployment catheter sheath, said self-expanding stent having, a generally cylindrical wire mesh stent operable for self-expansion deployment at a stenotic site within a patient's blood lumen, a generally cylindrical stent deployment cover coaxially extending over said self-expanding wire mesh stent, said stent deployment cover being operable to be axially withdrawn from engagement with said self-expanding wire mesh stent to permit said self-expanding stent to expand within a patient's stenotic blood lumen site; at least one of a low pressure marker balloon assembly connected to said deployment catheter sheath located at a distal end of said self-expanding stent, said balloon assembly including, at least one of an inflatable, low pressure, arcuate balloon segment and inflatable, low pressure, arcuate balloon segments, said at least one of an inflatable, low pressure, arcuate balloon segment and inflatable, low pressure, arcuate balloon segments having a total circumferential extent less than or equal to three hundred forty degrees extending about said deployment catheter sheath, and said at least one of an inflatable, low pressure, arcuate balloon segment and inflatable, low pressure, arcuate balloon segments being generally axially located on said deployment catheter sheath at a distal end of said generally cylindrical self-expanding wire mesh stent; and at least one independent, low pressure, inflation conduit connected to said deployment catheter sheath and to said at least one of a low pressure, balloon segment and low pressure, balloon segments and being operable to be connected to a low pressure inflation source at a proximal end of said deployment catheter sheath for selective delivery of fluid under low pressure to said at least one, low pressure, balloon segment and low pressure, balloon segments.

2. An angioplasty self-expanding stent catheter apparatus including at least one of a low pressure marker balloon assembly for facilitating accurate placement of a self-expanding stent within a patient's stenotic lumen site as defined in claim 1 wherein said low pressure, balloon assembly having at least one of an inflatable arcuate balloon segment and inflatable arcuate balloon segments comprises:
at least one of an arcuate shaped balloon segment and arcuate shaped balloon segments mounted at a distal end of said low pressure, balloon assembly subtends an arc of at least approximately twenty degrees.

3. An angioplasty self-expanding stent catheter apparatus including at least one of a low pressure marker balloon assembly for facilitating accurate placement of a self-expanding stent within a patient's stenotic lumen site as defined in claim 1 wherein said low pressure, balloon assembly having at least one of an inflatable arcuate balloon segment and inflatable arcuate balloon segments comprises:
at least one of an arcuate shaped balloon segment and arcuate shaped balloon segments mounted at a distal end of said low pressure, balloon assembly subtends an arc of at least approximately sixty degrees.

4. An angioplasty self-expanding stent catheter apparatus including at least one of a low pressure marker balloon assembly for facilitating accurate placement of a self-expanding stent within a patient's stenotic lumen site as defined in claim 1 wherein said low pressure, balloon assembly having at least one of an inflatable arcuate balloon segment and inflatable arcuate balloon segments comprises:
at least one of an arcuate shaped balloon segment and arcuate shaped balloon segments mounted at a distal end of said low pressure, balloon assembly subtends an arc of at least approximately one hundred and twenty degrees.

5. An angioplasty self-expanding stent catheter apparatus including at least one of a low pressure marker balloon assembly for facilitating accurate placement of a self-expanding stent within a patient's stenotic lumen site as defined in claim 1 wherein said low pressure, balloon assembly having at least one of an inflatable arcuate balloon segment and inflatable arcuate balloon segments comprises:
at least one low pressure fluid conduit connected to and generally co-extensive with said deployment catheter sheath and one conduit extending to each of said at least one arcuate shaped balloon segment and arcuate shaped balloon segments generally at a distal end of said deployment catheter sheath and being operable at a proximal end of said deployment catheter sheath for each low pressure fluid conduit to be connection to a source of low pressure fluid for selectively inflating said at least one arcuate shaped, low pressure, balloon segment and arcuate shaped, low pressure, balloon segments.

6. An angioplasty self-expanding stent catheter apparatus including at least one of a low pressure marker balloon assembly for facilitating accurate placement of a self-expanding stent within a patient's stenotic lumen site as defined in claim 1 wherein said low pressure, balloon assembly having at least one of an inflatable arcuate balloon segment and inflatable arcuate balloon segments comprises:

at least two independent and symmetrically opposing arcuate shaped, low pressure balloon segments mounted generally at a distal end of said deployment catheter sheath.

7. An angioplasty self-expanding stent catheter apparatus including at least one of a low pressure marker balloon assembly for facilitating accurate placement of a self-expanding stent within a patient's stenotic lumen site as defined in claim 6 wherein said low pressure, balloon assembly having at least one of an inflatable arcuate balloon segment and inflatable arcuate balloon segments comprises:

each of said two independent and symmetrically opposing arcuate shaped, low pressure, balloon segments mounted generally at the distal end of said deployment catheter sheath subtends an arc of at least approximately one hundred twenty degrees.

8. An angioplasty self-expanding stent catheter apparatus including at least one of a low pressure marker balloon assembly for facilitating accurate placement of a self-expanding stent within a patient's stenotic lumen site as defined in claim 6 wherein said low pressure, balloon assembly having at least one of an inflatable arcuate balloon segment and inflatable arcuate balloon segments comprises:

each of said two independent and symmetrically opposing arcuate shaped low pressure balloon segments mounted generally at the distal end of said deployment catheter sheath subtends an arc of at least approximately sixty degrees.

9. An angioplasty self-expanding stent catheter apparatus including at least one of a low pressure marker balloon assembly for facilitating accurate placement of a self-expanding stent within a patient's stenotic lumen site as defined in claim 6 wherein said low pressure, balloon assembly having at least one of an inflatable arcuate balloon segment and inflatable arcuate balloon segments comprises:

each of said two independent and symmetrically opposing arcuate shaped low pressure balloon segments mounted generally at the distal end of said deployment catheter sheath subtends an arc of at least approximately twenty degrees.

10. An angioplasty self-expanding stent catheter apparatus including at least one of a low pressure marker balloon assembly for facilitating accurate placement of a self-expanding stent within a patient's stenotic lumen site as defined in claim 6 wherein said low pressure, balloon assembly having at least one of an inflatable arcuate balloon segment and inflatable arcuate balloon segments comprises:

two, low pressure, fluid conduits generally co-extensive with said deployment catheter sheath and one fluid conduit independently extending to each of said two arcuate shaped, low pressure, balloon segments generally at a distal end of said deployment catheter sheath and being operable at a proximal end of said deployment catheter sheath for connection to a source of low pressure fluid for selectively and independently inflating each of said two arcuate shaped, low pressure, balloon segments.

11. An angioplasty self-expanding stent catheter apparatus including a low pressure balloon assembly for facilitating accurate placement of a self-expanding stent within a patient's stenotic lumen site, said site located in an iliac artery at the point where the iliac artery branches from a base of an aorta, said angioplasty self-expanding stent catheter apparatus comprising: a deployment catheter sheath having a proximal end and a distal end and being operable to be extended over a guide wire during a patient stenting procedure; a self-expanding stent connected generally at a distal end of said deployment catheter sheath, said self-expanding stent having, a generally cylindrical wire mesh stent operable for self-expansion deployment at a stenotic site within a patient's blood lumen, and a generally cylindrical stent deployment cover extending coaxially over said self-expanding wire mesh stent, said stent deployment cover being operable to be axially withdrawn from engagement with said self-expanding wire mesh stent to permit said self-expanding stent to expand within a patient's stenotic blood lumen site; a low pressure balloon assembly connected to said deployment catheter sheath located at a distal end of said self-expanding stent, said balloon assembly including, at least one of a selectively inflatable, low pressure, arcuate, balloon segment and inflatable, low pressure, balloon segments each being located at generally a distal end of said deployment catheter sheath, and said at least one of an inflatable, low pressure, arcuate, balloon segment and inflatable, low pressure, arcuate, balloon segments each having a total circumferential extent less than or equal to three hundred forty degrees extending about said deployment catheter sheath; and an independent, low pressure, inflation conduit connected to each of said at least one low pressure, balloon segment and low pressure, balloon segments and each conduit being operable to be connected to a low pressure inflation source at a proximal end of said deployment catheter sheath for selective delivery of fluid under low pressure to said at least one, low pressure, inflatable, balloon segment and low pressure, inflatable, balloon segments.

12. An angioplasty self-expanding stent catheter apparatus including a low pressure balloon assembly for facilitating accurate placement of a self-expanding stent within a patient's stenotic lumen site as defined in claim 11 wherein said at least one of a selectively inflatable, low pressure, balloon segment, and inflatable, low pressure, arcuate, balloon segments comprises:

at least two independent and symmetrically opposing, arcuate shaped, balloon segments mounted generally at a distal end of said deployment catheter sheath.

13. An angioplasty self-expanding stent catheter apparatus including a low pressure balloon assembly for facilitating accurate placement of a self-expanding stent within a patient's stenotic lumen site as defined in claim 12 wherein said at least two independent and symmetrically opposing, arcuate shaped, balloon segment, and inflatable, low pressure, arcuate, balloon segments comprises:

each of said two independent and symmetrically opposing, arcuate shaped, balloon segments mounted at a distal end of said deployment catheter assembly subtends an arc of at least one hundred and twenty degrees.

14. An angioplasty self-expanding stent catheter apparatus including a low pressure balloon assembly for facilitating accurate placement of the self-expanding stent within a patient's stenotic lumen site as defined in claim 13 wherein said low pressure, balloon assembly having at least one low pressure inflation conduit comprises:

two, low pressure, fluid conduits connected to and generally co-extensive with said deployment catheter sheath and one fluid conduit independently extending to each of said two, arcuate shaped, balloon segments generally at a distal end of said deployment catheter sheath and being operable at a proximal end of said deployment catheter sheath for connection to a source of low pressure fluid for selectively and independently inflating each of said two arcuate shaped, low pressure, balloon segments.

\* \* \* \* \*